US012672909B2

(12) United States Patent
Eilers

(10) Patent No.: US 12,672,909 B2
(45) Date of Patent: Jul. 7, 2026

(54) SCISSOR STYLE VESSEL SEALER

(71) Applicant: Conmed Corporation, Utica, NY (US)

(72) Inventor: Derek Eilers, Denver, CO (US)

(73) Assignee: Conmed Corporation, Utica, NY (US)

( * ) Notice: Subject to any disclaimer, the term of this patent is extended or adjusted under 35 U.S.C. 154(b) by 857 days.

(21) Appl. No.: 17/286,208

(22) PCT Filed: Oct. 21, 2019

(86) PCT No.: PCT/US2019/057212
§ 371 (c)(1),
(2) Date: Apr. 16, 2021

(87) PCT Pub. No.: WO2020/082067
PCT Pub. Date: Apr. 23, 2020

(65) Prior Publication Data
US 2021/0338312 A1 Nov. 4, 2021

Related U.S. Application Data

(60) Provisional application No. 62/747,725, filed on Oct. 19, 2018.

(51) Int. Cl.
*A61B 18/00* (2006.01)
*A61B 18/14* (2006.01)
(Continued)

(52) U.S. Cl.
CPC .......... *A61B 18/1442* (2013.01); *A61B 90/03* (2016.02); *A61B 2018/00404* (2013.01);
(Continued)

(58) Field of Classification Search
CPC ................ A61B 18/1442; A61B 90/03; A61B 2018/00404; A61B 2018/0063;
(Continued)

(56) References Cited

U.S. PATENT DOCUMENTS

| | | |
|---|---|---|
| 7,563,269 B2 | 7/2009 | Hashiguchi |
| 9,566,084 B2 | 2/2017 | Katsumata |

(Continued)

FOREIGN PATENT DOCUMENTS

| | | |
|---|---|---|
| EP | 2243439 A1 | 10/2010 |
| JP | 2016504153 | 2/2016 |

(Continued)

OTHER PUBLICATIONS

JP Office Action, App. No. 2021-521054, dated Apr. 6, 2022, pp. 1-14.
(Continued)

*Primary Examiner* — Tan-Uyen T Ho
*Assistant Examiner* — Lindsey R. Rivers
(74) *Attorney, Agent, or Firm* — Bond, Schoeneck & King, PLLC; David L. Nocilly

(57) ABSTRACT
An electrosurgical device having a first shaft with a tang positioned along an intermediate portion to provide a pivot point that is offset from the longitudinal axis. A second shaft is pivotally coupled to the tang of the first shaft using a slot that accepts the tang of the first shaft. The second shaft is formed from three portions, each of which extends along a different longitudinal axis so that the jaws of the device will be closed when the second shaft abuts a stop of the first shaft.

2 Claims, 5 Drawing Sheets

(51) Int. Cl.

| | | |
|---|---|---|
| *A61B 90/00* | (2016.01) | |
| *A61B 17/00* | (2006.01) | |
| *A61B 17/28* | (2006.01) | |
| *A61B 18/12* | (2006.01) | |

(52) U.S. Cl.
CPC . *A61B 2018/0063* (2013.01); *A61B 2018/146* (2013.01); *A61B 2090/035* (2016.02)

(58) Field of Classification Search
CPC ........ A61B 2018/146; A61B 2090/035; A61B 18/1412; A61B 2018/00601; A61B 2018/1455; A61B 2017/00738; A61B 2017/2926; A61B 2017/2919; A61B 2017/32113; A61B 2017/32004; A61B 2017/320069; A61B 2017/320074; A61B 2017/320075; A61B 2017/320077; A61B 2017/320082; A61B 2017/320092; A61B 2017/320093; A61B 17/2816; A61B 17/32; A61B 17/3201
See application file for complete search history.

(56) References Cited

U.S. PATENT DOCUMENTS

| | | | |
|---|---|---|---|
| 2004/0193199 A1 | 9/2004 | Hashiguchi | |
| 2005/0154387 A1* | 7/2005 | Moses ............... | A61B 17/2812 606/171 |
| 2009/0149854 A1 | 6/2009 | Cunningham et al. | |
| 2012/0083827 A1* | 4/2012 | Artale .................. | A61B 17/285 606/207 |
| 2015/0080925 A1 | 3/2015 | Schulte et al. | |
| 2016/0175033 A1 | 6/2016 | Le | |
| 2016/0183964 A1 | 6/2016 | Katsumata | |
| 2017/0105754 A1 | 4/2017 | Boudreaux et al. | |
| 2017/0296218 A1* | 10/2017 | Siebel ................ | A61B 17/2841 |
| 2019/0105100 A1* | 4/2019 | Bucciaglia ......... | A61B 18/1445 |

FOREIGN PATENT DOCUMENTS

| | | | |
|---|---|---|---|
| JP | 2016529927 | 9/2016 | |
| KR | 1020160039630 A | 4/2016 | |
| WO | WO-2015041846 A2 * | 3/2015 | ......... A61B 17/2816 |

OTHER PUBLICATIONS

International Search Report Form PCT/ISA/220, International Application No. PCT/US2019/057212, pp. 1-8, Dated Feb. 5, 2020.
Korean Office Action, Application No. 10-2021-7013191, pp. 3-9, Dated Jan. 19, 2023.
EP Office Action, Application No. 19802356.6, dated Dec. 5, 2024, entire document.

* cited by examiner

SCISSOR STYLE VESSEL SEALER

CROSS-REFERENCES TO RELATED APPLICATIONS

This application is a national stage application under 35 U.S.C. 371 based on international patent application PCT/US19/57212 filed on Oct. 21, 2019, which claims priority to U.S. Provisional Patent Application Ser. No. 62/747,725 filed on Oct. 19, 2018, the entireties of which are incorporated herein by reference.

BACKGROUND OF THE INVENTION

1. Field of the Invention

The present invention relates to electrosurgical vessel sealers and, more specifically, to a vessel sealer having an offset pivot for improved ergonomics.

2. Description of the Related Art

Electrosurgical vessel sealers are used for the occlusion of blood vessels and halting of bleeding during surgical procedures. The jaws of the vessel sealer are interconnected to an electrosurgical generator that can selective supply radiofrequency (RF) energy to the jaws for the desiccation and sealing of a blood vessel that has been clamped between the jaws. Conventional vessel sealers have jaws that can hinge in response to user activation. For example, the jaws may be positioned on the ends of shafts that are connected to a common hinge pin so that the jaws scissor in response to user movement of handles or finger grips positioned at the other ends of the shaft. This structural arrangement is mechanically inefficient, however, due to a loss of energy and unbalanced forces that lead to inefficient clamping and user hand fatigue. Accordingly, there is a need for improved hinging of the vessel sealer that provides for efficient mechanical clamping while optimizing user ergonomics. For open procedures, there is also a need to maximize the field of view at the jaw tips. Scissor style devices can be bulky, decreasing the surgeon's field of view in certain orientations.

Most vessel sealing devices also divide tissue using a blade that the surgeon can deploy manually by manipulating a trigger. Upon deployment with the jaws in a clamped position, the blade travels down the center of both jaws through a knife track. In devices that pivot on an axis that is on the same plane as the clamping (sealing surface), the blade travel through the center of the pivot. In order to provide clearance for a slot for the blade to protrude through and provide ample mechanical stability, the pivot diameter is large (6-7 mm) requiring a wide section around the pivot to contain it.

BRIEF SUMMARY OF THE INVENTION

The present invention is a vessel sealer having efficient clamping while providing an ergonomic design. The electrosurgical device comprises a first shaft extending along a longitudinal axis from a first end to a second and having a jaw associated with the first end. The first shaft includes a tang positioned along an intermediate portion thereof that is offset from the longitudinal axis. A second shaft extends from a first end to a second and has a second jaw associated with the first end. The second shaft is pivotally coupled to the tang of the first shaft. The second shaft includes a slot having a predetermined length accepting the pivot of the first shaft. The second shaft includes a first portion that extends along a first axis from the second end to the slot. The second shaft includes a second portion that extends along a second axis for the predetermined length of the slot. The second shaft includes a third portion that extends along a third axis from the slot to the first end. The second shaft includes a pair of sidewalls defining the slot. A pivot pin extends through the pair of sidewalls of the second shaft and the tang of the first shaft. A stop is positioned along the second shaft. The first axis, the second axis, and the third axis of the second shaft are oriented so that when the first jaw and the second jaw are in contact with each other the first portion of the second shaft is in contact with the stop of the first shaft. An electrosurgical controller is mounted to the first shaft and supporting the stop.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
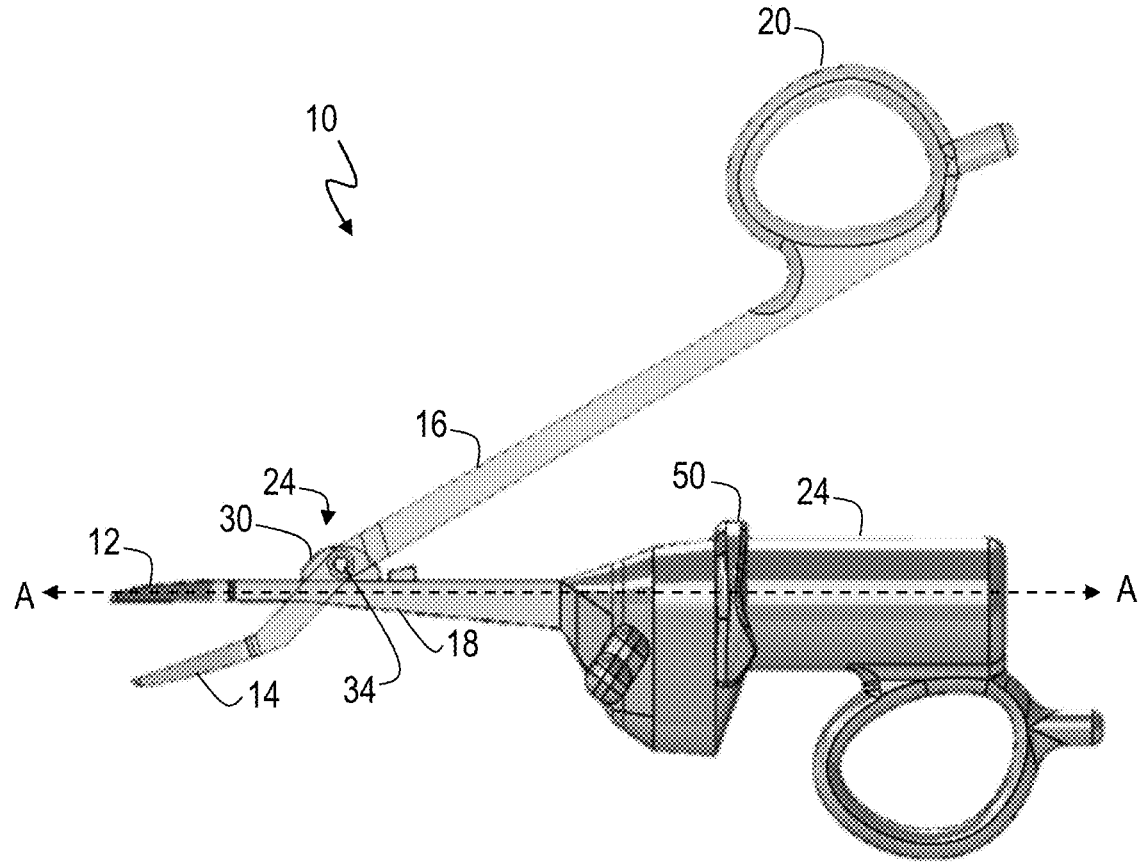
FIG. 1 is a side view of a vessel sealer according to the present invention.
Figure 2:
FIG. 2 is an opposing side view of a vessel sealer according to the present invention.

Referring to the figures, wherein like numeral refer to like parts throughout, there is seen in FIGS. 1 and 2 a vessel sealer 10 according to the present invention. Vessel sealer 10 comprises a pair of jaws 12 and 14, each of which is mounted to an end of a corresponding shaft 16 and 18. The opposing ends of shafts 16 and 18 form user handles and thus may include finger holes 20 and 22 mounted to each of shafts 16 and 18 to allow for easy grasping by a user. Shafts 16 and 18 are pivotally coupled to each other at an intermediate portion thereof by a pivot 24. As should be recognized by those of skill in the art, vessel sealer 10 is operated by driving the finger holes 20 and 22 in a scissoring motion to selectively open and close jaws 12 and 14. An electrosurgical controller 24 may be mounted to shaft 18 to provide radiofrequency (RF) energy to jaws 12 and 14 and to allow a user to selectively energize jaws 12 and 14 to perform electrosurgical operations when jaws 12 and 14 are closed about tissue to be treated.

Pivot 24 comprises a tang 30 extending transversely from a longitudinal axis A-A of shaft 18. Tang 30 includes a pivot pin 34 that extends through tang 30 and outwardly in both directions to engage shaft 18. Shaft 18 is substantially linear such that pivot 34 is offset from longitudinal axis A-A of shaft 18. Shaft 16 extends along a first longitudinal axis X-X from finger hole 20 to a point proximate to pivot 24.

Figure 3:
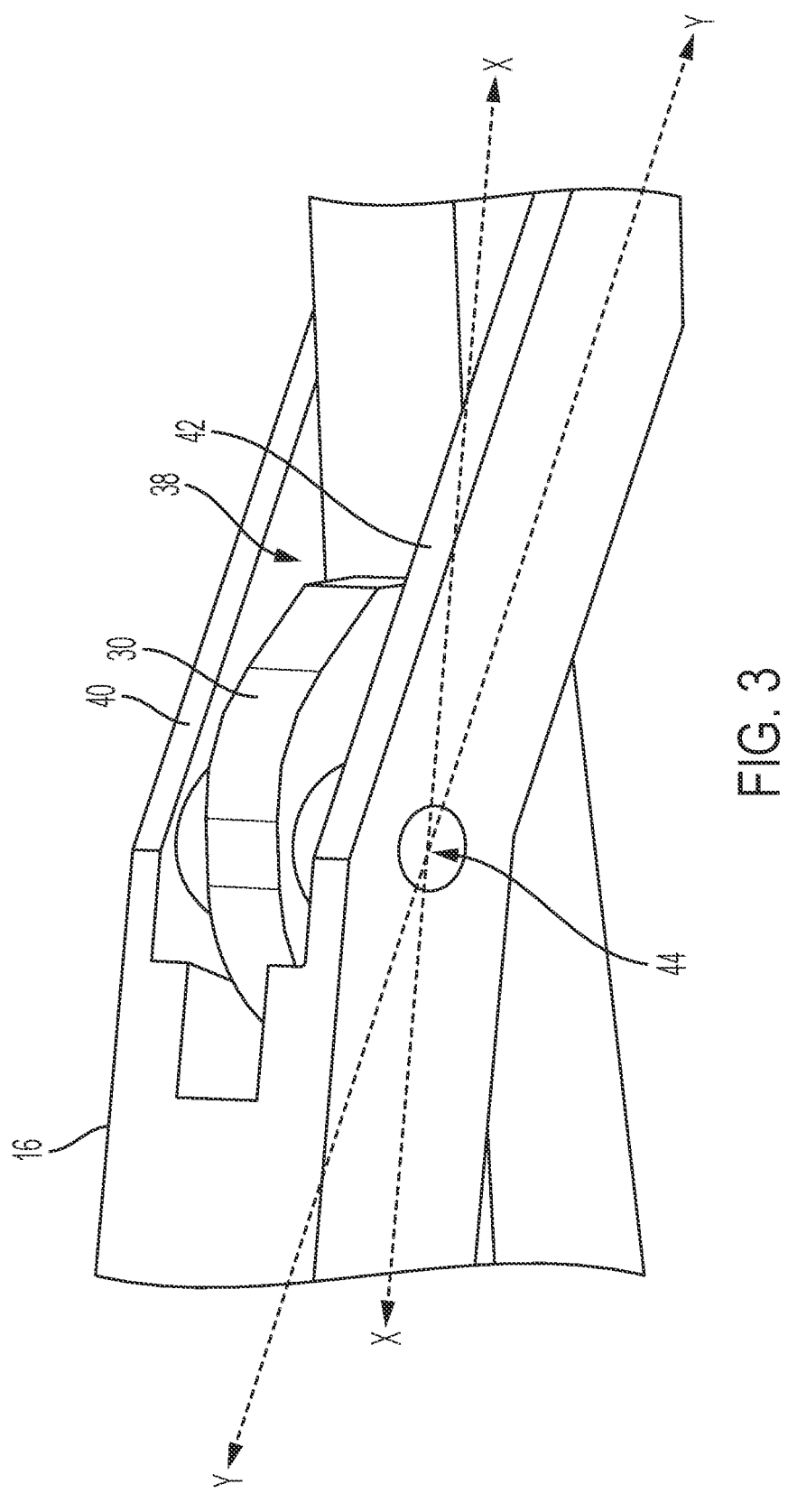
FIG. 3 is a first perspective view of an offset pivot for a vessel sealer according to the present invention.
Figure 4:
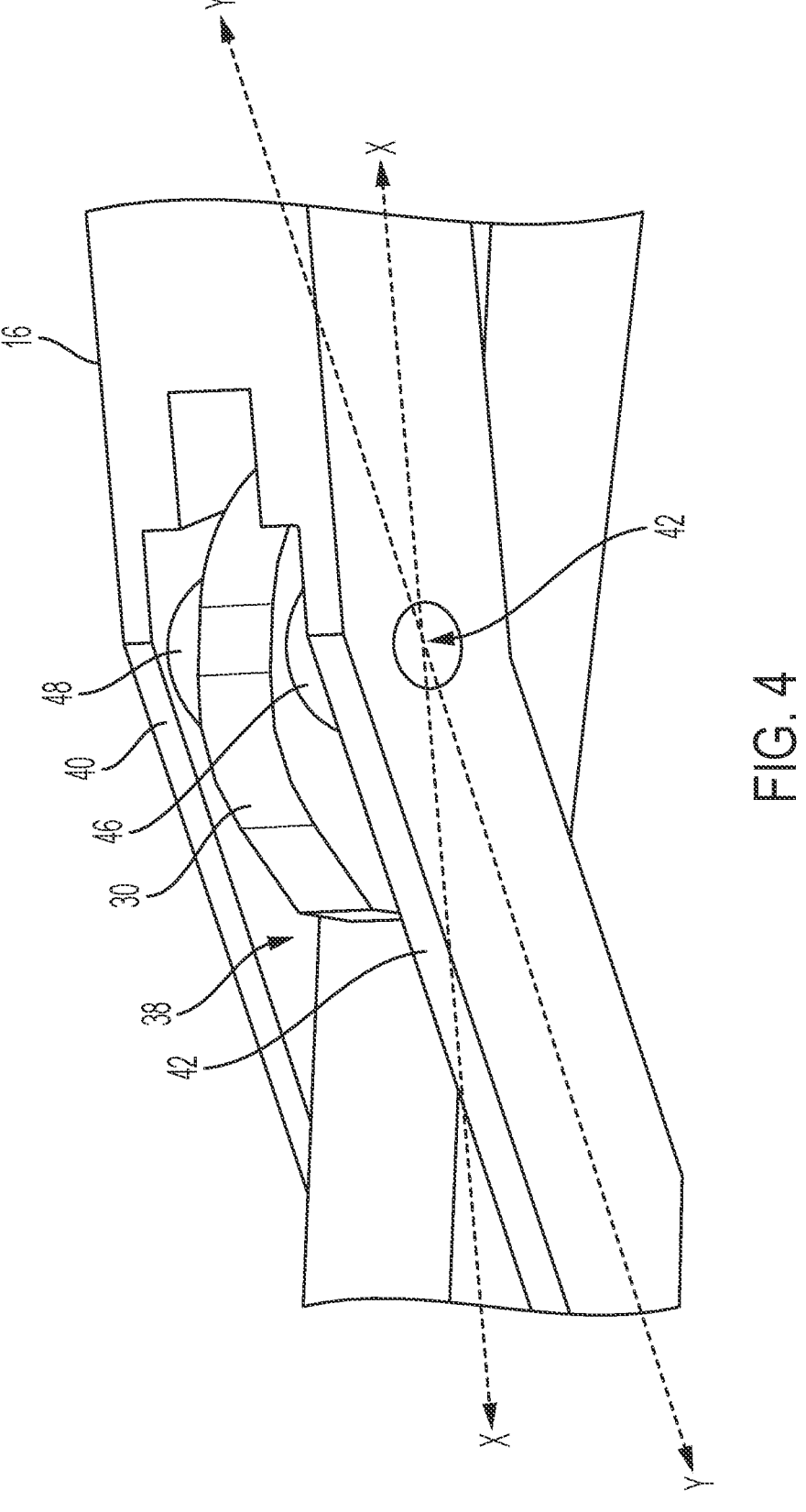
FIG. 4 is a second perspective view of an offset pivot for a vessel sealer according to the present invention.
Figure 5:
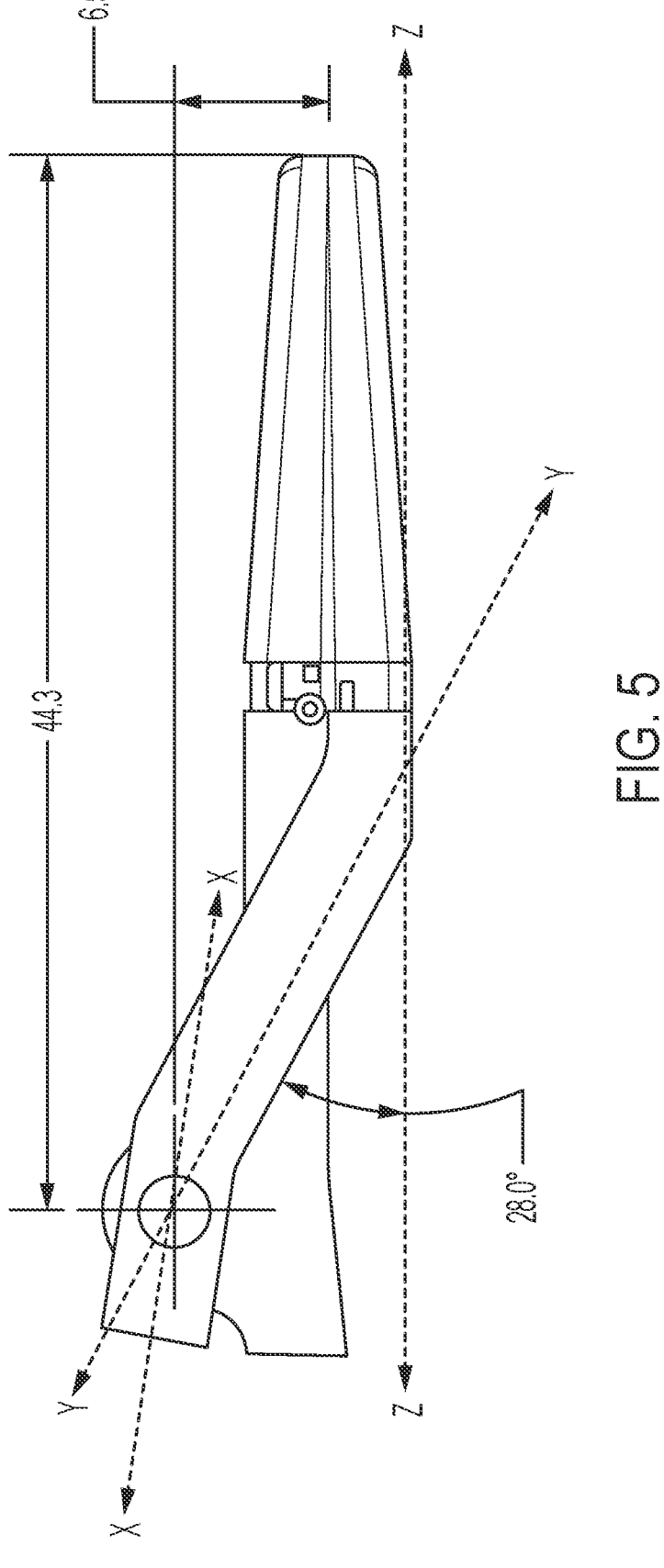
FIG. 5 is a side view of the shafts of a vessel sealer according to the present invention.

Referring to FIGS. 3 and 4, Shaft 16 includes a longitudinal slot 38 formed therethrough to define two opposing sidewalls 40 and 42. Slot 38 is dimensioned to accept tang 30 so that sidewalls 40 and 42 are positioned on either side of tang 30. Sidewalls 40 and 42 include corresponding pivot holes 42 and 44 for accepting pivot pin 34, thereby pivoting coupling shaft 16 to shaft 18. A pair of bushings 46 and 48 may be positioned in slot 38 about pivot pin 34 to engage and support the coupling of shafts 16 and 18 to each other. From pivot holes 42 and 44, sidewalls 40 and 42 of shaft 18 extends along a second longitudinal axis Y-Y that is oblique to axis X-X. At a point proximate to jaws 12 and 14, sidewalls 40 and 42 join together to close slot 38 and extend along a third axis Z-Z that is oblique to both axis X-X and axis Y-Y. As seen in FIG. 2, axis X-X, axis Y-Y, and axis Z-Z are positioned relative to each other so that jaws 12 and 14 will fully engage each other at the point where shafts 16 and 18 have pivoted so that shaft 16 has just contacted a stop 50 associated with shaft 18, shown as being positioned on a side of electrosurgical controller 24. There is seen in FIG. 5, the preferred angular relationship for axis Z-Z relative to axis Y-Y for a device having the particular dimensions, in inches, which are shown in FIG. 5. More specifically, the angle between axis Z-Z and Y-Y is about 28 degrees for an overall jaw length of 44.3 millimeters with an offset between the pivot and jaw centerline of 6.5 millimeters.

The offset 34 pivot of the present invention reduces the bulkiness of device 10, increasing the surgeon's field of view in certain orientations (as compared to a pivot that is centered). In addition, offsetting the pivot can allows for the use of a smaller diameter pin for the shafts to rotate about (e.g. 2 mm), thereby reducing the bulkiness of the device and providing a location for blade travel if desired.

What is claimed is:

1. An electrosurgical device, comprising:

a first shaft extending along a longitudinal axis from a first end to a second end, and having a first jaw associated with the first end, wherein the first shaft includes a tang positioned along an intermediate portion thereof that is offset from the longitudinal axis; and a second shaft extending from a first end of the second shaft to a second end of the second shaft, and having a second jaw associated with the first end, a slot having a predetermined length accepting a pivot of the first shaft, a first portion that extends along a first axis from the second end to the slot, a second portion that extends along a second axis that is oblique to the first axis for the predetermined length of the slot, a third portion that extends along a third axis that is oblique to the first axis from the slot to the first end; and a stop protruding from and positioned along the first shaft;

wherein the second shaft is pivotally coupled to the tang of the first shaft by a pivot pin extending through a pair of sidewalls of the second shaft, the tang of the first shaft, and a pair of bushings positioned in the slot;

wherein the pair of sidewalls join together and extend along the third axis that is oblique to the first axis and the second axis and are spaced apart from the pivot pin to provide a location where any blade extending along the third axis can travel along the third axis without contacting the pivot pin;

wherein the second axis and third axis are oriented at about 28 degrees relative to each other;

wherein the first jaw and the second jaw are interconnected to an electrosurgical generator that can selectively supply radiofrequency (RF) energy to the jaws for the desiccation and sealing of a blood vessel that has been clamped between the first jaw and the second jaw; and wherein the first axis, the second axis, and the third axis of the second shaft are oriented so that when the first jaw and the second jaw are in contact with each other an outside of the first portion of the second shaft is in contact with the stop of the first shaft.

2. The electrosurgical device of claim 1, further comprising an electrosurgical controller mounted to the first shaft and supporting the stop.

* * * * *